(12) United States Patent
Chhabra

(10) Patent No.: US 10,552,579 B1
(45) Date of Patent: Feb. 4, 2020

(54) MEDICATION DELIVERY SYSTEM

(71) Applicant: McKesson Corporation, San Francisco, CA (US)

(72) Inventor: Akhil Chhabra, Atlanta, GA (US)

(73) Assignee: MCKESSON CORPORATION, San Francisco, CA (US)

( * ) Notice: Subject to any disclaimer, the term of this patent is extended or adjusted under 35 U.S.C. 154(b) by 576 days.

(21) Appl. No.: 15/087,506

(22) Filed: Mar. 31, 2016

(51) Int. Cl.
  *G06F 19/00* (2018.01)
  *G06Q 10/06* (2012.01)
  *H04L 29/06* (2006.01)

(52) U.S. Cl.
  CPC ........ *G06F 19/3456* (2013.01); *G06F 19/328* (2013.01); *G06Q 10/0633* (2013.01); *H04L 63/10* (2013.01)

(58) Field of Classification Search
  CPC .............. G06F 19/3456; G06F 19/328; G06Q 10/0633; H04L 63/10; G16H 20/70; G16H 20/90
  See application file for complete search history.

(56) References Cited

U.S. PATENT DOCUMENTS

| | | | | |
|---|---|---|---|---|
| 7,734,483 B1* | 6/2010 | Smith | ................... | G06F 19/328 705/3 |
| 7,739,127 B1* | 6/2010 | Hall | ...................... | G06F 19/328 705/2 |
| 8,060,379 B1* | 11/2011 | Pinsonneault | ......... | G06Q 30/06 705/2 |
| 2015/0178685 A1* | 6/2015 | Krumel | .............. | G06Q 10/1057 705/322 |
| 2015/0269695 A1* | 9/2015 | Pinsonneault | ..... | G06Q 30/0207 705/2 |

* cited by examiner

*Primary Examiner* — Michael Tomaszewski
*Assistant Examiner* — Mohmad Muqueeth
(74) *Attorney, Agent, or Firm* — Alston & Bird LLP

(57) ABSTRACT

An improved medical delivery system increases the efficiency of acquiring and delivery savings to patients. The improved medical delivery system can reduce the potential for a pharmacy to fail to capture a financial benefit that may be available to the patient. The improved medical delivery system can provide a pharmacy improved systems for capturing patient financial benefits during a typical workflow process, and route the savings to the patient. The improved medical delivery system can also reduce the resources necessary for a pharmacy to acquire and provide a financial benefit to a patient.

20 Claims, 6 Drawing Sheets

MEDICATION DELIVERY SYSTEM

TECHNICAL FIELD

Aspects of the disclosure relate generally to medication delivery, and more particularly, to systems and methods for an improved medication delivery system.

BACKGROUND

A healthcare provider, such as a pharmacy, pharmacist, doctor's office, urgent care center, physician, hospital, or the like provides numerous healthcare related products and services to patients, including providing prescription products (e.g., medications, devices, etc.) or services to a patient. Typically, the healthcare provider relies on internal resources to provide patients with financial benefits offered by various programs (e.g., pharma manufacturers, a not-for profit entity, etc.) for a prescribed product. For example, the healthcare provider is required to identify and populate enrollment forms on behalf of the patient, a process that is typically performed outside a pharmacy workflow. Furthermore, the research required by the healthcare provider to identify the optimal program is cumbersome and does not guarantee a capture of the all the available benefit options for the patient. This type of manual process, requiring the healthcare provider to waste manpower on investigating savings options for the patient, can result in a significant loss on the part of the pharmacy and pharmacy resources. Thus, the inability for the typical pharmacy system to automatically and efficiently acquire savings for a patient during a prescription claim adjudication process presents a less than optimal patient result.

BRIEF DESCRIPTION OF THE DRAWINGS

Reference will now be made to the accompanying drawings, which are not necessarily drawn to scale, and wherein.

DETAILED DESCRIPTION OF EXAMPLE EMBODIMENTS

Figure 1:
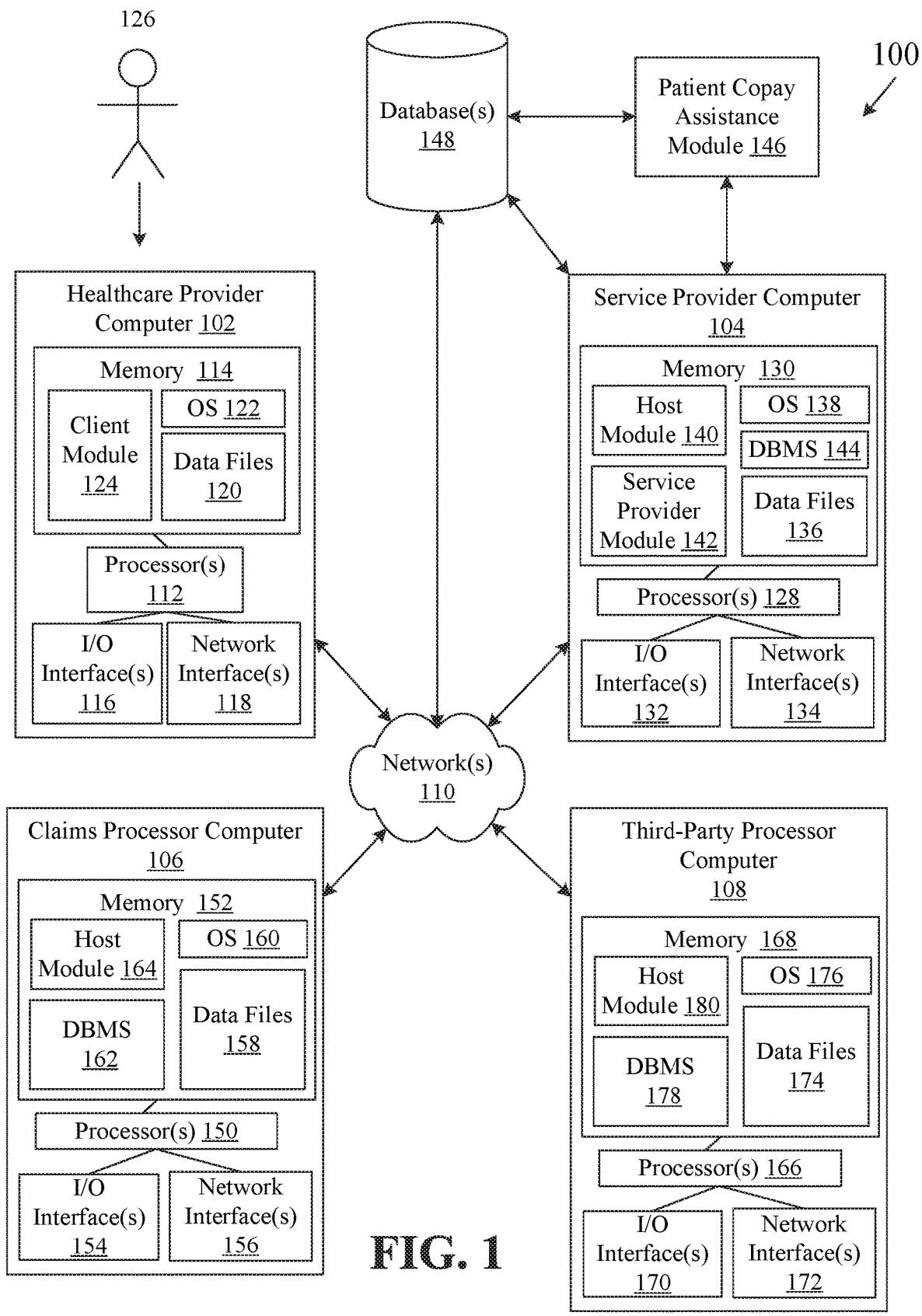
FIG. 1 illustrates an example overview of a system that facilitates an improved medical delivery system according to one exemplary embodiment.

Exemplary embodiments will now be described more fully hereinafter with reference to the accompanying drawings, in which example embodiments are shown. The concepts disclosed herein may, however, be embodied in many different forms and should not be construed as limited to the example embodiments set forth herein; rather, these embodiments are provided so that this disclosure will be thorough and complete, and will fully convey the scope of the concepts to those skilled in the art. Like numbers refer to like, but not necessarily the same or identical, elements throughout.

Example embodiments described herein include systems and methods that facilitate an improved medical delivery system as part of or in-line with the processing of one or more types of healthcare claim requests, such as a prescription claim request/transaction, prescription billing request, or medical claim transaction, in real-time or near real-time. For example, healthcare claim requests may be received electronically and automatically evaluated by a service provider computer to determine whether a financial benefit may be available for one or more of the pharmacy or prescribed product (e.g., medication, device, etc.) or service, identified in the healthcare claim request.

The service provider computer may electronically transmit the healthcare claim request to a claims processor computer (e.g., a pharmacy claims processor computer) for adjudication and receive back from the claims processor computer an adjudicated healthcare claim request response. The service provider computer may determine if the request was approved/paid. Based on the adjudicated healthcare claim request being approved/paid, the service provider computer can determine, based on information in the adjudicated healthcare claim request response, if the prescribed product or service is eligible for one or more financial benefits. The service provider computer may automatically access one or more financial benefit tables to ascertain whether a financial benefit may be available for the prescribed product or service.

Based at least in part upon a determination that a financial benefit is available in a first set of financial benefit tables, the service provider computer may apply the financial benefit to the adjudicated healthcare claim request response. The service provider computer may insert a financial benefit message and/or code into the adjudicated healthcare claim request response and communicate the adjudicated healthcare claim request response to the healthcare provider computer. However, if a financial benefit is not available in a first set of financial benefit tables, the service provider computer may automatically access a second set of financial benefit tables. The service provider computer may then determine if a financial benefit is available in the second set of financial benefit tables. If a financial benefit is available, the service provider computer may electronically transmit the adjudicated healthcare claim request response to a third-party processor computer for application of the financial benefit. The third-party processor computer may communicate a modified adjudicated healthcare claim request response to the service provider computer. The service provider computer may insert a financial benefit message and/or code into the modified adjudicated healthcare claim request response and communicate the adjudicated healthcare claim request response to the healthcare provider computer.

Based at least in part upon a determination that a financial benefit is not available in the second set of financial benefit tables, the service provider computer may access a third set of financial benefit tables to ascertain whether a financial benefit is available for the prescribed product or service. The service provider computer may compile a list of any financial benefits identified in the third set of financial benefit tables for the identified product or service. The compiled list may be inserted as a financial benefit message and/or code into the adjudicated healthcare claim request response and electronically transmitted to the healthcare provider computer. The healthcare provider computer may receive the compiled list of financial benefits and provide the list to a patient. If the patient opts to receive one of the financial benefits from the compiled list, a pharmacist or pharmacy employee may utilize the healthcare provider computer to enroll the patient in the patient selected financial benefit.

The service provider computer may receive a secondary healthcare claim request from the healthcare provider computer. The service provider computer may electronically transmit the secondary healthcare claim request to a claims processor computer (e.g., a pharmacy claims processor computer) for adjudication and receive back from the claims processor computer a secondary adjudicated healthcare claim request response. The service provider computer may determine if the request was approved/paid. Based on the secondary adjudicated healthcare claim request being approved/paid, the service provider computer can electronically transmit the secondary adjudicated healthcare claim transaction response to the healthcare provider computer.

System Overview

FIG. 1 illustrates an example system 100 supporting an improved medical delivery system according to one example embodiment. The exemplary system 100 facilitates the implementation of the improved medical delivery system as part of or in-line with the processing of healthcare claim requests and will now be described illustratively with respect to FIG. 1. As shown in FIG. 1, the system 100 may include at least one healthcare provider computer 102, at least one service provider computer 104, a patient copay assistance module 146, at least one claims processor computer 106 (e.g., a pharmacy claims processor computer), and at least one third-party processor computer 108 (e.g., a coupon card processor computer).

As desired, each of the healthcare provider computer 102, service provider computer 104, patient copay assistance module 146, claims processor computer 106, and/or third-party processor computer 108 may include one or more processing devices that may be configured for accessing and reading associated computer-readable media having stored thereon data and/or computer-executable instructions for implementing the various methods disclosed in the exemplary embodiments discussed herein.

Additionally, in certain exemplary embodiments, the service provider computer 104 and/or the patient copay assistance module 146 may be in communication with one or more data storage devices, such as a database 148. The database 148 may receive, store, and provide, as needed, patient copay assistance data from the service provider computer 104 and/or the patient copay assistance module 146. In certain exemplary embodiments, the healthcare claim transaction data includes all or any portion of the data included in healthcare claim transactions received by the service provider computer 104 from a healthcare provider computer 102 and/or adjudicated healthcare claim transaction responses adjudicated by a claims processor computer 106 or a third-party processor computer 108. In addition, the database 148 or another database may include schedules, tables or listings of service provider sponsored patient financial benefits available for medications or other healthcare products; schedules tables, or listings of third-party sponsored financial benefits available for medications or other healthcare products; schedules, tables or listing of patient reimbursement financial benefits available for medications or other healthcare products. These records can include at least the drug identifier (e.g., NDC), a sponsor identifier (e.g., a third-party processor identifier), a financial benefit amount, and the like. Alternatively, the data storage function may be included in the service provider computer 104 and/or the patient copay assistance module 146 itself, such as in the memory 130 of the service provider computer 104.

Generally, network devices and systems, including one or more of the healthcare provider computers 102, service provider computer 104, patient copay assistance module 146, claims processor computer 106, and third-party processor computer 108 may include or otherwise be associated with suitable hardware and/or software for electronically transmitting and receiving data and/or computer-executable instructions over one or more communications links or networks. These network devices and systems may also include any number of processors for processing data and executing computer-executable instructions, as well as other internal and peripheral components that are well known in the art. Further, these network devices and systems may include or be in communication with any number of suitable memory devices operable to store data and/or computer-executable instructions. By executing computer-executable instructions, each of the network devices form a special purpose computer or particular machine. As used herein, the term "computer-readable medium" describes any form of suitable memory or memory device.

As shown in FIG. 1, the healthcare provider computer 102, service provider computer 104, claims processor computer 106, third-party processor computer 108, patient copay assistance module 146, and database 148 may be in communication with each other via one or more networks, such as network 110, which as described below can include one or more separate or shared private and public networks, including the Internet or a publicly switched telephone network. Each of these components, the healthcare provider computer 102, service provider computer 104, claims processor computer 106, third-party processor computer 108, patient copay assistance module 146, database 148, and the network 110 will now be discussed in further detail.

Each healthcare provider computer 102 may be associated with (e.g., located within and/or providing computing services for) a pharmacy or other healthcare provider, such as, for example, a pharmacy, physician's office, hospital, clinic, etc. While the exemplary healthcare provider computer 102 will be described as within or part of a pharmacy or pharmacy practice management system with regard to the methods of FIGS. 3A-C, this is for example only and is not intended to be limiting in any manner. Each healthcare provider computer 102 may be any suitable processor-driven device that facilitates the processing of healthcare requests made by patients or consumers and the communication of information associated with healthcare claim requests to the healthcare provider computer 102, such as a server computer, a mainframe computer, one or more networked computers, a desktop computer, a personal computer, a digital assistant, a personal digital assistant, a digital tablet, an Internet appliance, an application-specific circuit, microcontroller, minicomputer, or any other processor-based device. In certain embodiments, each healthcare provider computer 102 may be a suitable point-of-sale device located within a pharmacy. The execution of the computer-implemented instructions by the healthcare provider computer 102 forms a special-purpose computer or other particular machine that is operable to facilitate the processing of healthcare requests made by patients and the communication of information associated with healthcare claim requests to a healthcare provider computer 102. Additionally, in certain example embodiments, the operations and/or control of each healthcare provider computer 102 may be distributed amongst several processing components.

In addition to having one or more processors 112, each healthcare provider computer 102 may include one or more memory devices 114, one or more input/output ("I/O") interfaces 116, and one or more network interfaces 118. The memory devices 114 may be any suitable memory device, for example, caches, read-only memory devices, random access memory devices, magnetic storage devices, removable storage devices, etc. The memory devices 114 may store data, executable instructions, and/or various program modules utilized by the healthcare provider computer 102, for example, data files 120, an operating system ("OS") 122, and/or a client module 124, respectively. The data files 120 may include any suitable data that facilitates the receipt and/or processing of healthcare requests by the healthcare provider computer 102 and the generation and/or processing of healthcare claim requests that are communicated to the service provider computer 104. For example, the data files 132 may include, but are not limited to, healthcare information and/or contact information associated with one or more patients, information associated with the particular healthcare provider and/or the respective healthcare provider computer 102, information associated with the service provider computer 104, information associated with one or more claims processors (e.g., payor identifiers such as Banking Identification Numbers (BIN Numbers), Processor Control Numbers (PCNs), and Group IDs), information associated with one or more third-party processor computers 108 (e.g., third-party identifier), and/or information associated with one or more healthcare claim requests. The OS 122 may be any suitable software module that controls the general operation of the healthcare provider computer 102. The OS 122 may also facilitate the execution of other software modules by the one or more processors 112, for example, the client module 124. The OS 122 may be any currently existing or future-developed operating system including, but not limited to, Microsoft Windows®, Apple OSX™, Linux, Unix, or a mainframe operating system.

The client module 124 may be an Internet browser or other suitable software, including a dedicated program, for interacting with the service provider computer 104. For example, a user 126 such as a pharmacist, pharmacy assistant, nurse practitioner, physician, nurse, or other pharmacy, hospital, physician's office, or other healthcare provider employee may utilize the client module 124 in preparing and electronically transmitting a healthcare claim request, such as a prescription claim request/transaction, prescription billing request, or medical claim transaction, to the service provider computer 104 for delivery to the appropriate claims processor computer 106, third-party processor computer 108, or other third-party for adjudication or other coverage/benefits determination. The healthcare provider computer 102 may also utilize the client module 124 to retrieve or otherwise receive data, messages, or responses from the service provider computer 104 and/or other components of the system 100. For example, in certain example embodiments, the client module 124 may be utilized to receive a rejection of the healthcare claim request, and/or an adjudicated healthcare claim request response from the service provider computer 104 as will be described below.

The one or more I/O interfaces 116 may facilitate communication between the healthcare provider computer 102 and one or more input/output devices, for example, one or more user interface devices, such as, a display, keypad, keyboard, control panel, touch screen display, remote control, mouse, microphone, etc. that facilitate user interaction with the healthcare provider computer 102. For example, the one or more I/O interfaces 116 may facilitate entry of information associated with a healthcare claim request by an employee 126 of a pharmacy, such as a pharmacy employee, pharmacist, hospital employee, or nurse practitioner affiliated with a pharmacy, hospital, physician's office or other similar healthcare provider. The one or more network interfaces 118 may facilitate connection of the healthcare provider computer 102 to one or more suitable networks, for example, the network 110 illustrated in FIG. 1. In this regard, the healthcare provider computer 102 may receive and/or communicate information to other network components of the system 100, such as the service provider computer 104.

With continued reference to FIG. 1, the service provider computer 104 may include, but is not limited to, any suitable processor-driven device that is configured for receiving, processing, and fulfilling requests from the one or more healthcare provider computers 102, the patient copay assistance module 146, the database 148, the claims processor computer 106, and/or the third-party processor computer relating to pharmacy, benefits (e.g., patient copay assistance), billing, electronic prescription submission, and/or other healthcare claim requests and/or other activities. In certain exemplary embodiments, the service provider computer 104 may be a switch/router that routes healthcare claim requests and/or other healthcare requests from a pharmacy to a claims processor and/or other third-party processor. For example, the service provider computer 104 may route healthcare claim requests communicated from the healthcare provider computer computer 102 (at e.g., a pharmacy) to a claims processor computer 106, such as a pharmacy benefits manager (PBM), an insurer, a Medicare payor, other governmental healthcare insurance payor, or other third-party payor. In yet another example, the service provider computer 104 may route healthcare claim requests communicated from the healthcare provider computer 102 to a third-party processor computer 108, such as a coupon card processor or other third-party coupon adjudicator.

In certain embodiments, the service provider computer 104 may include a suitable host server, host module, or other software that facilitates the receipt of a healthcare claim request from a healthcare provider computer 102 and/or the routing of the received healthcare claim request to a claims processor computer 106 or a third-party processor computer 108. Any number of healthcare provider computers 102, patient copay assistance module 146, databases 148, claims processor computers 106, and/or third-party processor computers 108 may be in communication with the service provider computer 104, via the network 110 for example, as desired in various embodiments.

The service provider computer 104 may include any number of special purpose machines. In certain example embodiments, the operations of the service provider computer 104 may be controlled by computer-executed or computer-implemented instructions that are executed by one or more processors associated with the service provider computer 104 to form the special purpose computer or machine that is operable to facilitate the receipt, evaluation, editing, routing, and/or other processing of electronic healthcare requests. The one or more processors that control the operations of the service provider computer 104 may be incorporated into the service provider computer 104 and/or in communication with the service provider computer 104 via one or more suitable networks. In certain exemplary embodiments, the operations and/or control of the service provider computer 104 may be distributed amongst several processing components.

Similar to the healthcare provider computer 102 described above, the service provider computer 104 may include one or more processors 128, one or more memory devices 130, one or more input/output ("I/O") interfaces 132, and one or more network interfaces 134. The one or more memory devices 130 may be any suitable memory devices, for example, caches, read only memory devices, random access memory devices, magnetic storage devices, removable memory devices, etc. The one or more memory devices 130 may store data, executable instructions, and/or various program modules utilized by the service provider computer 104, for example, data files 136, an operating system ("OS") 138, the host module 140, a service provider module 142, and a database management system ("DBMS") 144 to facilitate management of data files 136 and other data stored in the memory devices 130. The OS 138 may be a suitable software module that controls the general operation of the service provider computer 104 and/or that facilitates the execution of other software modules. The OS 138 may be any currently existing or future-developed operating system including, but is not limited to, Microsoft Windows®, Apple OSX™, Linux, Unix, or a mainframe operating system.

The service provider module 142 may be operable to perform one or more pre-edits or pre-analysis on a received healthcare claim request prior to routing or otherwise communicating the received healthcare claim request, such as a prescription claim request/transaction, to a suitable claims processor computer 106 or a suitable third-party processor computer 108. Additionally, the service provider module 142 may be operable to perform one or more post-edits on an adjudicated reply or response that is received from a claims processor computer 108 and/or a third processor computer 108 for a healthcare claim request prior to routing the adjudicated response to one of the healthcare providers 102. In one example embodiment, the service provider module may be operable to parse the healthcare claim request and/or adjudicated healthcare claim request response to determine one or more of the pharmacy identifier, prescribed product (e.g., medications, devices, etc.) or sponsor identifier, reject code/message, product/service cost, and transaction code and can determine if the pharmacy identified by the pharmacy identifier, the prescribed product (e.g., medication, device, etc.), service, or medication class identified by the prescribed product or service identifier, the reject type or basis for rejection, the product or service cost and/or the transaction type identified by the transaction code, a financial benefit amount applicable to the product or service cost, and/or a financial benefit sponsor available for the product or service. The service provider module 142 may be further operable to insert a financial benefit message and/or code into the healthcare claim request and can electronically transmit or facilitate the transmission of the financial benefit message to the healthcare provider computer 102. In certain example embodiments, the patient copay assistance module 146 or a combination of the patient copay assistance module 146 and the service provider module 142 may also be operable to perform the functions described with reference to the service provider module 142 herein. A wide variety of different pre-edits and/or post-edits may also be performed by the service provider module 156 as desired in various embodiments of the disclosure.

According to one exemplary embodiment, the data files 136 may store healthcare claim request records associated with communications received from various healthcare provider computers 102, and/or various claims processor computers 106, and/or various third-party processor computers 108. The data files 136 may also store any number of suitable routing tables that facilitate determining the destination of communications received from a healthcare provider computer 102, claims processor computer 106, and/or a third-party processor computer 108. In certain example embodiments, the data discussed herein that is included in the database 148 may alternatively be stored and accessed from the data files 136. For example, the data files 136 may also store schedules, tables or listings of service provider sponsored patient financial benefits available for medications or other healthcare products identified in the healthcare request; schedules tables, or listings of third-party sponsored financial benefits available for medications or other healthcare products identified in the healthcare request; schedules, tables or listing of patient reimbursement financial benefits available for medications or other healthcare products identified in the healthcare request. These records can include at least the drug identifier (e.g., NDC), a sponsor identifier (e.g., a third-party processor identifier), a financial benefit amount, and the like. The exemplary data files 136 may also store records containing, for example, patient identification data, healthcare claim requests, tables identifying pharmacies, prescribed product (e.g., medications, devices, etc.) or service identifiers, override codes, payor identifiers, and transaction type codes.

The host module 140 may receive, process, and respond to requests from the client module 124 of the healthcare provider computer 102, may receive, process, and respond to requests of the patient copay assistance module 146, may further receive, process, and respond to requests of the host module 164 of the claims processor computer 106, and may further receive, process, and respond to requests of the host module 180 of the third-party processor computer 108. The service provider computer 104 may include additional program modules for performing other processing methods described herein. Those of ordinary skill in the art will appreciate that the service provider computer 104 may include alternate and/or additional components, hardware or software without departing from exemplary embodiments of the disclosure.

With continued reference to the service provider computer 104, the one or more I/O interfaces 132 may facilitate communication between the service provider computer 104 and one or more input/output devices, for example, one or more user interface devices, such as a display, keypad, keyboard, mouse, control panel, touch screen display, remote control, microphone, etc. that facilitate user interaction with the service provider computer 104. The one or more network interfaces 134 may facilitate connection of the service provider computer 104 to one or more suitable networks, for example, the network 110 illustrated in FIG. 1. In this regard, the service provider computer 104 may communicate with other components of the system 100.

One or more patient copay assistance modules 146 may also be operative with or included with the service provider computer 104. The patient copay assistance module 146 may include computer-executable instructions for facilitating selection and application of patient financial assistance for a prescribed product based on an inquiry of available financial benefits as part of the processing of a healthcare claim request. As an example, the patient copay assistance module 146 may be operative or configured to be operable to parse the healthcare claim request and/or adjudicated healthcare claim request response to determine one or more of the pharmacy identifier, prescribed product (e.g., medications, devices, etc.) or sponsor identifier, reject code/message, product/service cost, and transaction code and can determine if the pharmacy identified by the pharmacy identifier, the prescribed product (e.g., medication, device, etc.), service, or medication class identified by the prescribed product or service identifier, the reject type or basis for rejection, the product or service cost and/or the transaction type identified by the transaction code, a financial benefit type/amount applicable to the product or service cost, and/or a financial benefit sponsor available for the product or service. In one implementation, the patient copay assistance module 146 may parse an adjudicated prescription claim request response to identify the product and/or service (e.g., NDC) in the adjudicated prescription claim request response. The patient copay assistance module 146 may utilize the identified NDC, for example, to query one or more financial benefit tables and/or lists to determine whether a financial benefit exists for the identified NDC. For example, the patient copay assistance module 146 may identify the NDC in the adjudicated prescription claim request response to correlate to a specialty drug Granix™, a medication typically prescribed as a cancer support medication. While the following example is described with reference to a specialty drug, it is to be appreciated that any product and/or service may be identified. Continuing with the example implementation, the patient copay assistance module 146 may access at least one or more service provider sponsored benefit tables and/or lists, one or more third-party benefit tables and/or lists, and/or one or more patient reimbursement tables and/or lists to identify one or more financial benefits available for identified drug Granix™. If the financial benefit is a service provider sponsored benefit, the patient copay assistance module 146 may access and apply the financial benefit to the adjudicated prescription claim request response. For example, if the financial benefit is associated with reducing and/or eliminating a patient copay amount, the patient copay assistance module 146 may modify the patient pay amount in the adjudicated prescription claim request response to correspond to the financial benefit. The patient copay assistance module 146 or any other portion of the service provider computer 104 may be further operable to insert a financial benefit message and/or code into the adjudicated prescription claim request response. By way of yet another example, if the financial benefit is a third-party benefit, the patient copay assistance module 146 or any other portion of the service provider computer 104 (e.g., the service provider module 142) may electronically transmit or facilitate the transmission of the adjudicated prescription claim request response to a third-party adjudicator (e.g., third-party processor computer 108), for application of the financial benefit to the adjudicated prescription claim request response. By way of yet another example, if the financial benefit is a patient reimbursement financial benefit, the patient copay assistance module 146 may compile a list of available financial benefits for the identified product or service, such as Granix™. The compiled list may be inserted as a financial benefit message and/or code into the adjudicated prescription claim request response and electronically transmitted to the healthcare provider computer 102 for further processing.

In one example embodiment, the patient copay assistance module 146 may be implemented as computer-implemented instructions of the memory 130 of the service provider computer 104. Alternatively, the patient copay assistance module 146 may also be implemented as computer-implemented instructions of a memory of a separate processor-based system communicably coupled to the service provider computer 104, according to another example embodiment.

The database 148 of FIG. 1 represents one or more databases that can be locally or remotely distributed with respect to the service provider computer 104 and/or the patient copay assistance module 146. The database 148 may be operable to store information associated with various patients and/or from various healthcare claim requests that have been received by the service provider computer 104 and/or adjudicated healthcare claim request responses adjudicated by the one or more claims processor computers 108. The database 148 may also store schedules, tables or listings of service provider sponsored patient financial benefits available for medications or other healthcare products; schedules tables, or listings of third-party sponsored financial benefits available for medications or other healthcare products; schedules, tables or listing of patient reimbursement financial benefits available for medications or other healthcare products. These records can include at least the drug identifier (e.g., NDC), a sponsor identifier (e.g., a third-party processor identifier), a financial benefit amount, and the like.

With continued reference to FIG. 1, the claims processor computer 106 (e.g., a pharmacy claims processor computer for a pharmacy claims processor) may be any suitable processor-driven device that facilitates receiving, processing, and/or fulfilling healthcare claim requests, such as a prescription claim request/transaction, prescription billing request, or medical claim transaction, received from the service provider computer 104. For example, the claims processor computer 106 may be a processor-driven device associated with one or more PBMs, insurers, government payors, Medicare Part D payors, accountable care organizations, or claims clearinghouses. As desired, the claims processor computer 106 may include any number of special purpose computers or other particular machines, application-specific circuits, microcontrollers, personal computers, minicomputers, mainframe computers, servers, and the like.

In certain exemplary embodiments, the operations of the claims processor computer 106 may be controlled by computer-executed or computer-implemented instructions that are executed by one or more processors associated with the claims processor computer 106 to form a special purpose computer or other particular machine that is operable to facilitate the receipt, processing, and/or fulfillment of healthcare claim requests received from the service provider computer 104. The one or more processors that control the operations of the claims processor computer 106 may be incorporated into the claims processor computer 106 and/or in communication with the claims processor computer 106 via one or more suitable networks. In certain embodiments, the operations and/or control of the claims processor computer 106 may be distributed amongst several processing components.

Similar to other components of the system 100, the claims processor computer 106 may include one or more processors 150, one or more memory devices 152, one or more input/output ("I/O") interfaces 154, and one or more network interfaces 156. The one or more memory devices 152 may be any suitable memory devices, for example, caches, read-only memory devices, random access memory devices, magnetic storage devices, removable memory devices. The one or more memory devices 152 may store data, executable instructions, and/or various program modules utilized by the claims processor computer 106, for example, data files 158, an operating system ("OS") 160, a database management system ("DBMS") 162, and a host module 164. The data files 158 may include any suitable information that is utilized by the claims processor computer 106 to process healthcare claim requests, for example, patient profiles, patient insurance information, other information associated with a patient, information associated with a healthcare provider, etc. The OS 160 may be a suitable software module that controls the general operation of the claims processor computer 106. The OS 160 may also facilitate the execution of other software modules by the one or more processors 150, for example, the DBMS 162 and/or the host module 164. The OS 160 may be any currently existing or future-developed operating system including, but is not limited to, Microsoft Windows®, Apple OSX™, Linux, Unix, or a mainframe operating system.

The DBMS 162 may be a suitable software module that facilitates access and management of one or more databases that are utilized to store information that is utilized by the claims processor computer 106 in various example embodiments. The host module 164 may initiate, receive, process, and/or respond to requests, such as healthcare claim requests, from the host module 140 of the service provider computer 104. The claims processor computer 106 may include additional program modules for performing other pre-processing or post-processing methods described herein. Those of ordinary skill in the art will appreciate that the claims processor computer 106 may include alternate and/or additional components, hardware or software without departing from the example embodiments described herein.

The one or more I/O interfaces 154 may facilitate communication between the claims processor computer 106 and one or more input/output devices, for example, one or more user interface devices, such as a display, keypad, keyboard, mouse, control panel, touch screen display, remote control, microphone, etc. that facilitate user interaction with the claims processor computer 106. The one or more network interfaces 156 may facilitate connection of the claims processor computer 106 to one or more suitable networks, for example, the network 110. In this regard, the claims processor computer 106 may receive healthcare claim requests and/or other communications from the service provider computer 104 and the claims processor computer 106 may communicate information associated with processing the healthcare claim requests to the service provider computer 104.

With continued reference to FIG. 1, the third-party processor computer 108 (e.g., a third-party processor computer for a third-party coupon card processor) may be any suitable processor-driven device that facilitates receiving, processing, and/or fulfilling healthcare claim requests, such as a prescription claim request/transaction, prescription billing request, or medical claim transaction, received from the service provider computer 104. For example, the claims third-party processor computer 108 may be a processor-driven device associated with one or more coupon card processors operable to facilitate the application of one or more financial benefits to a healthcare claim request. As desired, the processor computer 108 may include any number of special purpose computers or other particular machines, application-specific circuits, microcontrollers, personal computers, minicomputers, mainframe computers, servers, and the like.

In certain exemplary embodiments, the operations of the third-party processor computer 108 may be controlled by computer-executed or computer-implemented instructions that are executed by one or more processors associated with the third-party processor computer 108 to form a special purpose computer or other particular machine that is operable to facilitate the receipt, processing, and/or fulfillment of healthcare claim requests received from the service provider computer 104. The one or more processors that control the operations of the third-party processor computer 108 may be incorporated into the third-party processor computer 108 and/or in communication with the third-party processor computer 108 via one or more suitable networks. In certain embodiments, the operations and/or control of the third-party processor computer 108 may be distributed amongst several processing components.

Similar to other components of the system 100, the third-party processor computer 108 may include one or more processors 166, one or more memory devices 168, one or more input/output ("I/O") interfaces 170, and one or more network interfaces 172. The one or more memory devices 168 may be any suitable memory devices, for example, caches, read-only memory devices, random access memory devices, magnetic storage devices, removable memory devices. The one or more memory devices 168 may store data, executable instructions, and/or various program modules utilized by the third-party processor computer 108, for example, data files 174, an operating system ("OS") 176, a database management system ("DBMS") 178, and a host module 180. The data files 174 may include any suitable information that is utilized by the third-party processor computer 108 to process healthcare claim requests, for example, information associated with a financial benefit that may be applied to a healthcare request, such as, for example, a patient copay assistance, information associated with a third-party coupon card provider, etc. The OS 176 may be a suitable software module that controls the general operation of the third-party processor computer 108. The OS 176 may also facilitate the execution of other software modules by the one or more processors 166, for example, the DBMS 178 and/or the host module 180. The OS 176 may be any currently existing or future-developed operating system including, but is not limited to, Microsoft Windows®, Apple OSX™, Linux, Unix, or a mainframe operating system.

The DBMS 178 may be a suitable software module that facilitates access and management of one or more databases that are utilized to store information that is utilized by the third-party processor computer 108 in various example embodiments. The host module 180 may initiate, receive, process, and/or respond to requests, such as healthcare claim requests, from the host module 140 of the service provider computer 104, and/or the claims processor computer 106, and or the healthcare provider computer 102. The third-party processor computer 108 may include additional program modules for performing other pre-processing or post-processing methods described herein. Those of ordinary skill in the art will appreciate that the third-party processor computer may include alternate and/or additional components, hardware or software without departing from the example embodiments described herein.

The one or more I/O interfaces 170 may facilitate communication between the third-party processor computer 108 and one or more input/output devices, for example, one or more user interface devices, such as a display, keypad, keyboard, mouse, control panel, touch screen display, remote control, microphone, etc. that facilitate user interaction with the third-party processor 108. The one or more network interfaces 172 may facilitate connection of the third-party processor computer 108 to one or more suitable networks, for example, the network 110. In this regard, the third-party processor computer 108 may receive healthcare claim requests and/or other communications from the service provider computer 104 and/or the claims processor computer 106, and/or the healthcare provider computer 102, and the third-party processor computer 108 may communicate information associated with processing the healthcare claim requests to the service provider computer 104.

The network 110 may include any telecommunication and/or data network, whether public, private, or a combination thereof, including a local area network, a wide area network, an intranet, the Internet, intermediate hand-held data transfer devices, and/or any combination thereof and may be wired and/or wireless. The network 110 may also allow for real-time, off-line, and/or batch transactions to be electronically transmitted between or among the healthcare provider computer 102, the service provider computer 104, the patient copay assistance module 146, the database 148, the claims processor computer 106, and/or the third-party processor computer 108. Due to network connectivity, various methodologies, as described herein may be practiced in the context of distributed computing environments. Although the service provider computer 104 is shown for simplicity as being in communication with the healthcare provider computer 102, the patient copay assistance module 146, the database 148, the claims processor computer 106, and/or the third-party processor computer 108 via one intervening network 110, it is to be understood that any other network configuration is possible. For example, intervening network 110 may include a plurality of networks, each with devices such as gateways and routers for providing connectivity between or among networks 110. Instead of or in addition to a network 110, dedicated communication links may be used to connect the various devices in accordance with an example embodiment. For example, the service provider computer 104 may form the basis of network 110 that interconnects one or more of the healthcare provider computer 102, the patient copay assistance module 146, the database 148, the claims processor computer 106, and the third-party processor computer 108.

Those of ordinary skill in the art will appreciate that the system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one exemplary embodiment, the service provider computer 104 (or other computer) may be implemented as a specialized processing machine that includes hardware and/or software for performing the methods described herein. Accordingly, the exemplary embodiments described herein should not be construed as being limited to any particular operating environment, system architecture, or device configuration.

Operational Overview

Figure 2A:
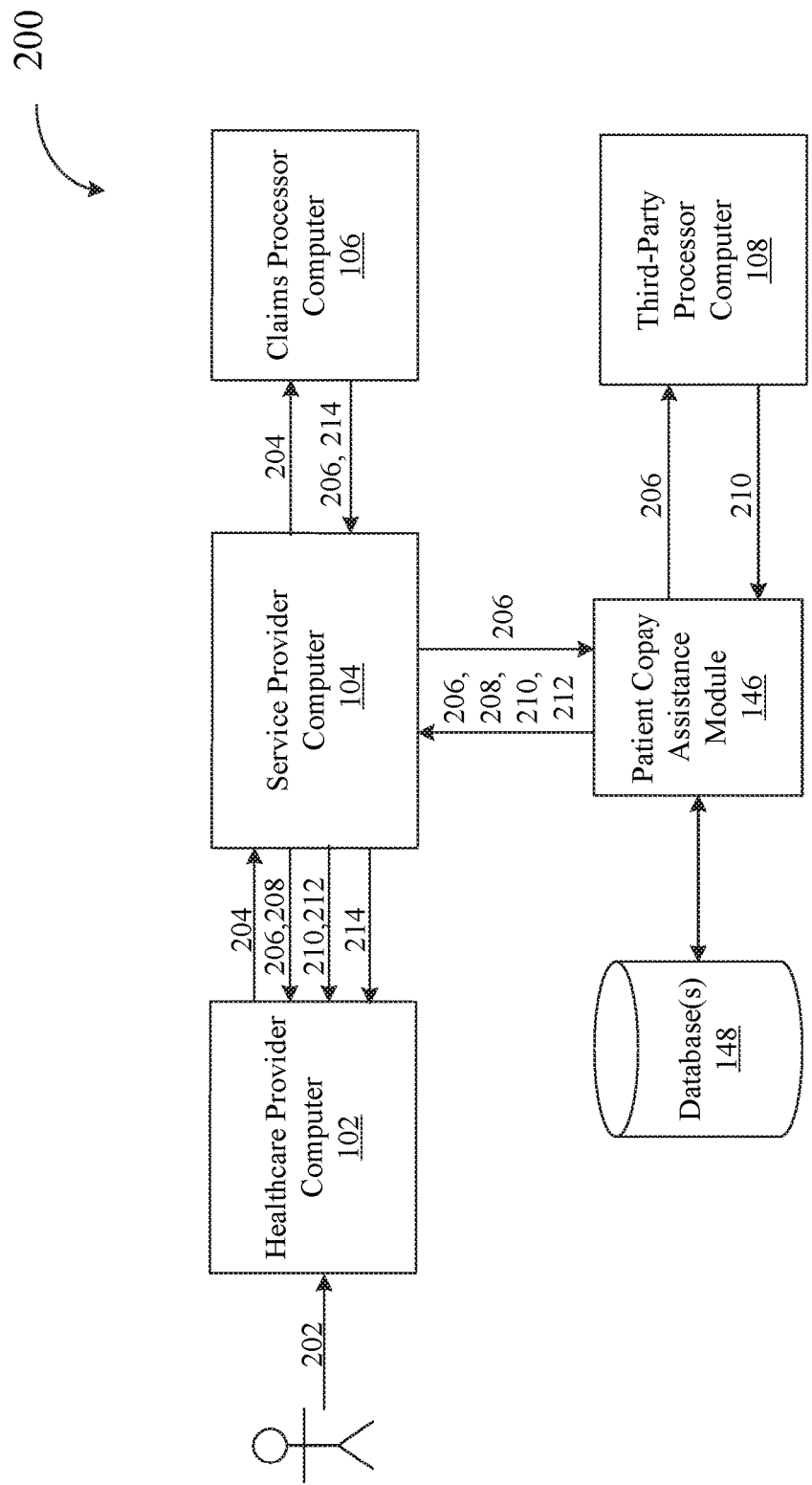
FIG. 2A is a diagram of an example system flow for the improved medical delivery system according to one exemplary embodiment.
Figure 3A:
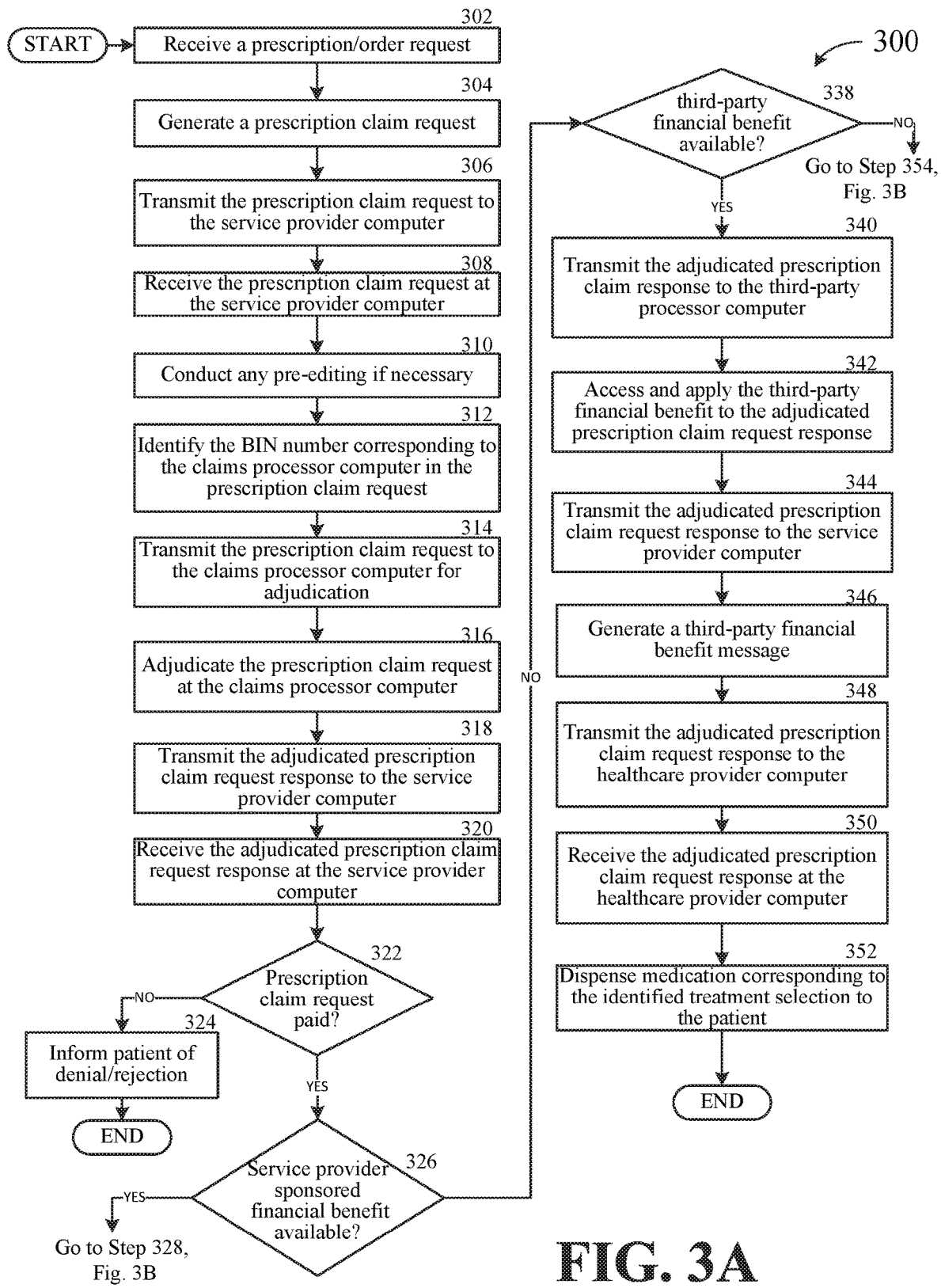
FIGS. 3A-3C are a flow chart of an example methodology for implementing the improved medical delivery system, in accordance with one exemplary embodiment.
Figure 3B:
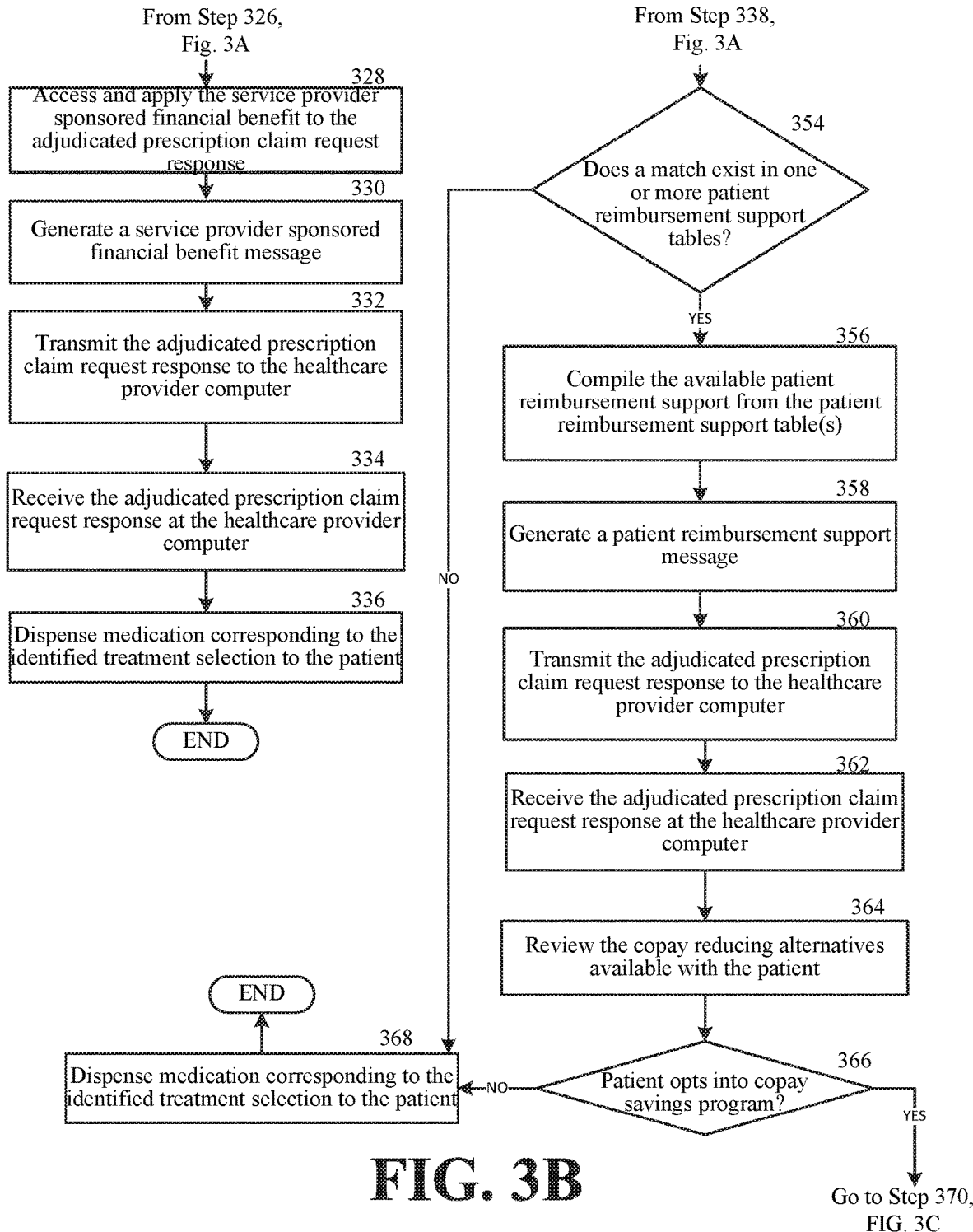
Figure 3C:
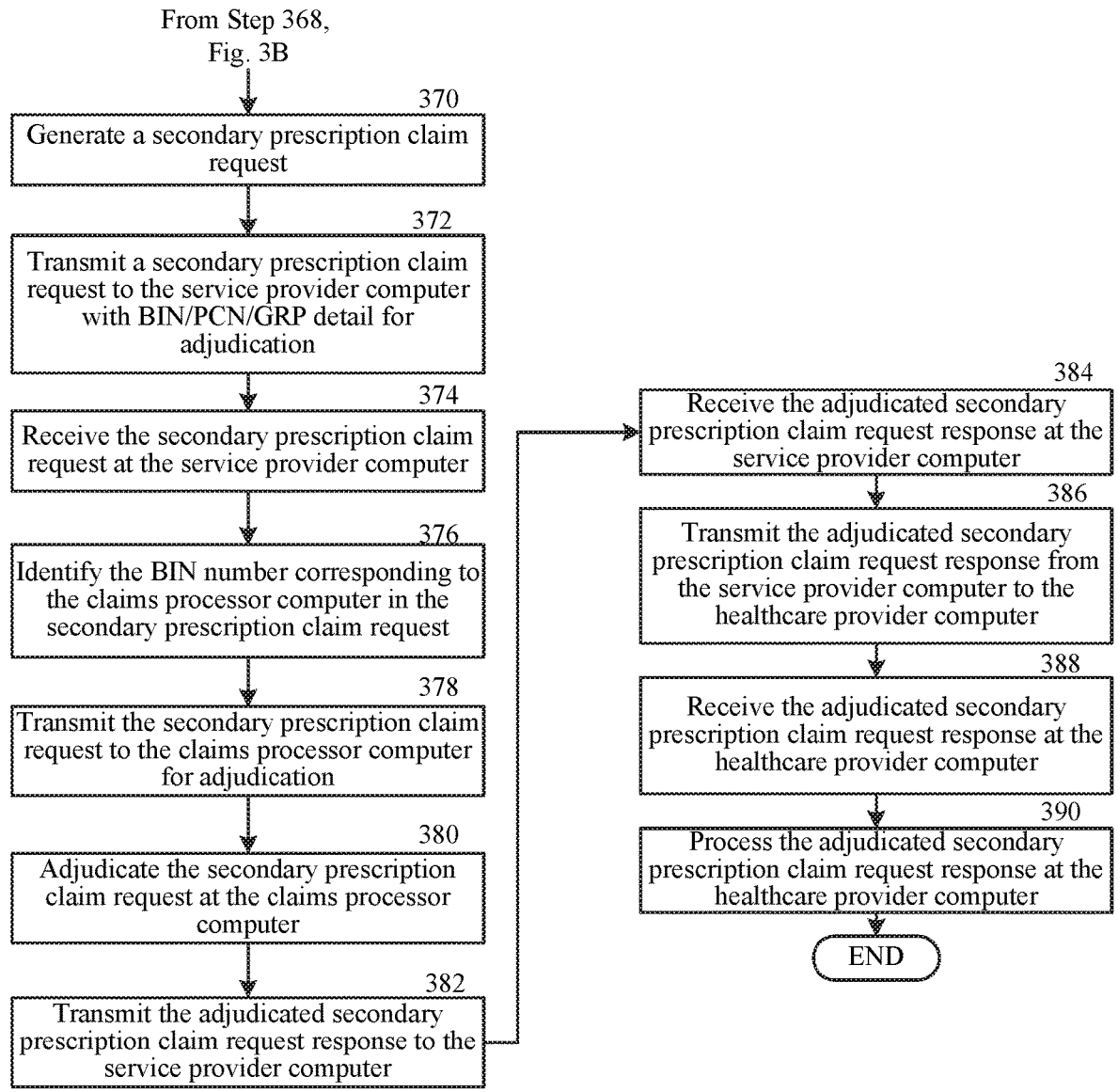

FIG. 2A is a diagram of one example system flow 200 for the improved medical delivery system as part of or in-line with the processing of a healthcare claim request through a service provider, such as through the service provider computer 104 illustrated in FIG. 1. FIGS. 3A-3C are flow charts of an example method 300 for implementing the improved medical delivery system as part of the processing of the healthcare claim request, such as a prescription claim request/transaction, prescription billing request, or medical claim transaction, in accordance with one exemplary embodiment. The exemplary method 300, described below, may be performed by a suitable service provider computer 104 and/or patient copay assistance module 146.

The exemplary method 300 will be described with reference to a pharmacy as the healthcare provider; however, this is only for purposes of example as other healthcare providers could be substituted for, and should each be individually read as being a part of each of these methods. As such, where the discussion of the methods below and the drawings state a pharmacy, any other healthcare provider could be substituted, such as a physician, hospital, physician's office, clinic, prescriber of the medication, or healthcare center. Furthermore, the exemplary methods will be described with reference to a pharmacy claims processor as the claims processor associated with the claims processor computer; however, this is also only for purposes of example as other claims processors and associated claims processor computers could be substituted for and should be each individually read as being part of each of these methods.

In addition, the exemplary method 300 described below will be described with reference to a prescription claim request as the healthcare claim request; however, this also is only for purposes of example as other healthcare claim requests (which may include, for example, a prescription claim request/transaction, prescription billing request, or medical claim transaction) could be substituted for the prescription claim request and each form of healthcare claim request should each individually be read as being used in the methods described below.

Referring now to FIGS. 1, 2A, and 3A-C, the exemplary method 300 begins at the START step and proceeds to step 302, where a prescription/order request 202 is received. In one example embodiment, the prescription/order request 202 is received by a pharmacist at a pharmacy. The prescription/order request 202 may be received from a patient, another healthcare provider prescribing a medication or service (e.g., physician, hospital, etc.), by phone, via the Internet, via an electronic prescription (i.e., electronic prescription order transaction, e-script, or e-prescription) or by way of an electronic system order. For example, the prescription 202 may be received by the patient from a prescriber of the medication, such as a doctor, dentist, nurse, or physician's assistant. The patient may go to the location of the pharmacy and physically hand the prescription request 202 to the pharmacist or make a request via a web portal communicably coupled to the healthcare provider computer 102 or an IVR communicably coupled or otherwise providing order data to the healthcare provider computer 102. The pharmacist determines the patient's name and accesses the healthcare provider computer 102, which receives a selection of patient information from the pharmacist via the I/O interface 116. For example, the pharmacist accesses the healthcare provider computer 102 and accesses a database of patient information, which may be stored in memory 116 or in another database either local or remote from the healthcare provider computer 102. The pharmacist can then select the name or other patient identification information in the patient information database that matches the name or other identification information of the patient. In certain example embodiments, this information from the database includes the payor identifier for the request, such as the Payor ID/routing information (e.g., BIN Number, BIN Number and PCN, and/or BIN Number and Group ID) that identifies the claims processor computer 106 intended to receive and adjudicate the prescription claim request 204.

In step 304, a prescription claim request 204 is generated and/or formatted at the healthcare provider computer 102. In certain exemplary embodiments, the healthcare provider computer 102 formats the prescription claim request 204 with patient information, payor identifier information, and prescribed product (e.g., medications, devices, etc.) or service information, the quantity of the product or service to be dispensed to the patient and the days' supply of the product or service that the patient will be receiving. The information can be input into the prescription claim request 204 by the pharmacist via the I/O interface 116 or automatically retrieved and entered by the healthcare provider computer 102 based at least in part on historical transaction information for the patient in the data files 120 or a database communicably coupled to the healthcare provider computer 102. According to one example embodiment, the prescription claim request 204 may be formatted in accordance with a version of the National Council for Prescription Drug Programs (NCPDP) Telecommunication Standard, although other standards may be utilized as well.

As discussed above, the prescription claim request 204 may include a BIN Number, a BIN Number and PCN, and/or a BIN Number and Group ID for identifying a particular claims processor computer (e.g., PBM, healthcare insurance company, Medicare or other government healthcare insurance payor, Medicare Part D provider, etc.), such as the claims processor computer 106, as a destination for the prescription claim request 204. In addition, the prescription claim request 204 may also include information relating to the patient, payor, prescriber, healthcare provider, and/or the requested product (e.g., medication or device) or service. As an example, the prescription claim request 204 may include one or more of the following information:

Payor identifier—Payor ID/Routing Information
BIN Number (i.e. Banking Identification Number), BIN Number and Processor Control Number (PCN) and/or BIN Number and Group ID, that designates a destination (e.g., the claims processor computer 106) of the prescription claim request 204
Patient Information
Name (e.g. Patient Last Name, Patient First Name, etc.)
Date of Birth of Patient
Age of Patient
Gender
Patient Address (e.g. Street Address, Zip Code, etc.)
Patient Contact Information (e.g. patient telephone number, email address, etc.)
Patient Health Condition Information
Patient ID or other identifier (e.g., Health Insurance Claim Number (HICN), social security number, etc.)
Insurance/Coverage Information
Cardholder Name (e.g. Cardholder First Name, Cardholder Last Name)
Cardholder ID and/or other identifier (e.g. person code)
Group ID and/or Group Information
Prescriber Information
Primary Care Provider ID or other identifier (e.g. NPI code)
Primary Care Provider Name (e.g. Last Name, First Name)
Prescriber ID or other identifier (e.g. NPI code, DEA number)
Prescriber Name (e.g. Last Name, First Name)
Prescriber Contact Information (e.g. Telephone Number)
Pharmacy Information
Pharmacy or other Healthcare Provider Information (e.g. store name, store address, chain identifier, etc.)
Pharmacy or other Healthcare Provider ID (e.g. NPI code)
Claim Information
Medication, service, or product information—Product (medication or device) or service identifier (e.g. National Drug Code (NDC code), RxNorm code, etc.), product or service name, etc.
Prescription/Service Reference Number
Date Prescription Written
Quantity Dispensed
Days' Supply
Diagnosis/Condition (e.g., diagnosis code)
Pricing information for the drug/service/product (e.g. ingredient cost (e.g., in an Ingredient Cost field), dispensing fee (e.g., in a Dispensing Fee field), gross amount due (e.g., in a Gross Amount Due field), and Usual and Customary Charge amount (e.g., in a Usual and Customary Charge field))
Number of Refills Authorized
Fill Number (i.e., the current refill number for the current request 204)
One or more NCPDP Message Fields
One or more Drug Utilization (DUR) Codes
Date of Service.

The prescription claim request 204 can be used to determine if the pharmacy claims processor associated with the claims processor computer 106 approves or rejects payment coverage for the prescribed product (e.g., medications, devices, etc.) or service being requested in the prescription claim request 204 and, if approved, the amount the pharmacy claims processor will cover (or pay) for the prescribed product (e.g., medication, device, etc.) or service being requested and how much the patient pay amount (the amount the patient is responsible to pay for) will be.

The healthcare provider computer 102 electronically transmits the prescription claim request 204 to the service provider computer 104 in step 306. In step 308, the service provider computer 104 receives the prescription claim request 204. For example, the prescription claim request 204 can be electronically transmitted by the healthcare provider computer 102 to the service provider computer 104 through the network 110. The service provider computer 104 conducts any pre-editing, if necessary, on the prescription claim request 204 in step 310. In one implementation, the pre-edits may include, without limitation, verifying, adding, and/or editing information included in the prescription claim request 204 prior to it being communicated to a claims processor computer 106 and/or a third-party processor 108. For example, the service provider computer 104 can parse the prescription claim request 204 to determine/edit the financial fields, the service code, the quantity dispensed, and or the Days' Supply of the product.

At step 312, the service provider computer 104 can parse the received prescription claim request 204 to determine the destination of the prescription claim request 204 (e.g., based on the Banking Identification Number (BIN Number), the BIN Number and Processor Control Number (PCN) or the BIN Number and Group ID in one or more fields of the prescription claim request 204).

The service provider computer 104 electronically transmits the prescription claim request 204 to the claims processor computer 106 in step 314. For example, a prescription claim request 204 can be electronically transmitted from the service provider computer 104 to the claims processor computer 106 via the network 110. The claims processor computer 106 receives and adjudicates the prescription claim request 204 in step 316 to determine if the patient has coverage, to determine to what extent the patient's coverage covers the requested product or service identified in the request 204, and to generate an adjudicated claim prescription request response 206 as to whether the request 204 is approved/paid or rejected. Example request responses in the adjudicated prescription claim request response 206 can include, but are not limited to, accepted, approved, paid, captured, denied (e.g., rejected), and denied (e.g., rejected) with request for additional information and resubmission. In certain exemplary embodiments, the request responses can be input into a field of the prescription claim request 204 that is recognized by the service provider computer 104 and/or the healthcare provider computer 102. Typically, if the request response for the request 204 is approved, the adjudicated prescription claim request response 206 provides the amount of the cost of the medication, product, or service that will be covered by the pharmacy claims processor associated with the pharmacy claims processor computer 108 (the total amount paid, which is provided in the Total Amount Paid field of the adjudicated prescription claim request response 206), any amount applied to a patient deductible which is provided in the amount applied to periodic deductible field of the adjudicated prescription claim request response 206), and the patient pay amount (which is provided in the Patient Pay Amount field of the adjudicated prescription claim request response 206). On the other hand, if the request response is a rejection, the adjudicated response 206 provides the reason for the rejection (e.g., in the form of a reject code, for example, patient not covered, Cardholder ID submitted in the request is inactive, prior authorization required, medication not covered, claim limit exceeded, quantity exceeded, days' supply exceeded, etc.).

In step 318, the claims processor computer 106 electronically transmits the adjudicated prescription claim request response 206 to the service provider computer 104 via, for example, the network 110. The service provider computer 104 receives the adjudicated prescription claim request response 206 from the claims processor computer 106 in step 320.

In step 322, an inquiry is conducted to determine if the adjudicated prescription claim request response 206 has a request response status indicating that the prescription claim request 204 was paid or rejected. In one exemplary embodiment, the service provider module 142 or another portion of the service provider computer 104 parses the adjudicated prescription claim request response 206 and identifies the code in the field associated with the request response status. The service provider computer 104 compares that identified code to a table of request response status codes in, for example, the database 148 or the data files 136 to determine the request response from the claims processor computer 106. If the request response status by the claims processor computer 106 is that the prescription claim request 204 is approved or paid, the YES branch is to step 326. On the other hand, if the request response status for the prescription claim request 204 was denied (rejected) or not paid, the NO branch is followed out of the current example process and the adjudicated prescription claim request response 206 is processed in a standard manner. For example, at step 324, if the prescription claim request 204 was denied/rejected, the pharmacist or other pharmacy employee may inform the patient of the denial/rejection and the basis for the denial/rejection included in the adjudicated prescription claim request response 206. The process may end following step 324.

In step 326, the service provider computer 104 conducts any post-editing, if necessary, on the adjudicated prescription claim request response 206. For example, the post-edits may include determining whether any service provider sponsored financial benefit(s), (e.g., an incentive program, such as a coupon, voucher, rebate, discount, loyalty award, or other equivalent non-insurance benefit or the like) is available for the patient and/or the prescribed product (e.g., medications, devices, etc.) or service identified in the adjudicated prescription claim request response 206. In one implementation, the determination of whether service provider sponsored non-insurance related financial benefits are available is based, at least in part, on information included in the adjudicated prescription claim request response 206. For example, the patient copay assistance module 146, and/or any other part of the service provider computer 104, may parse the adjudicated prescription claim request response 206 to identify a treatment selection in or more predetermined fields of the request. For example, the prescription selection may include, without limitation, a drug identifier (e.g., NDC code), a product name, an active ingredient name associated with a medication, and/or a drug product classification. The patient copay assistance module 146 and/or some other part of the service provider computer 104 may compare the drug identifier for the identified treatment selection in the adjudicated prescription claim request response 206 to one or more service provider sponsored financial benefit tables and/or lists stored in the database 148 and/or the data files 136. For example, an identified NDC may correspond to the drug Granix™. The patient copay assistance module 146 may compare the NDC for the drug Granix™ to the one or more service provider sponsored benefit tables and/or lists to determine if a financial benefit is available for the drug. In one implementation, the one or more service provider sponsored benefit tables and/or lists are organized according to product and/or service identifiers (e.g., NDC). A match between the drug identifier corresponding to the identified treatment selection (e.g., Granix™) and a drug identifier in the service provider sponsored financial benefit tables and/or lists may indicate that at least one service provider sponsored financial benefit (e.g., the availability of co-pay savings/reduction, standard co-pay saving cards, or other discount cards such as a first fill free associated with a specific treatment for the illness/disease, a fixed or percentage amount for a voucher, coupon, or discount available to the patient, etc.) associated with the treatment selection identified in the adjudicated prescription claim request response 206 may be available. If the service provider sponsored financial benefit tables and/or lists include a match corresponding to the drug identifier associated with the identified treatment selection, the YES branch is followed and processing may proceed to step 328. However, if it is determined that the service provider sponsored financial benefit tables and/or lists do not include a match corresponding to the drug identifier associated with the identified treatment selection, the NO branch is followed and processing may proceed to step 338.

In step 328, the patient copay assistance module 146 or another portion of service provider computer 104 may access the service provider sponsored financial benefit tables and/or lists stored in the database 148 and/or the data files 136 to ascertain and apply a financial benefit(s) (e.g., copay reductions, coupons, vouchers, standard copay saving cards, other discount cards, etc.) to the adjudicated prescription claim request response 206. For example, the service provider sponsored financial benefit may include a benefit to reduce and/or eliminate a patient copay amount owing for the identified treatment selection (e.g. Granix™). The patient copay assistance module 146 or another portion of service provider computer 104 may apply the financial benefit to the adjudicated prescription claim request response 206. For example, where the service provider sponsored financial benefit reduces and/or eliminates the patient copay amount, the patient copay assistance module 146 or another portion of service provider computer 104 may modify the adjudicated prescription claim request response 206 to reflect the service provider sponsored financial benefit.

In step 330, the patient copay assistance module 146 or another portion of the service provider computer 104 may generate a service provider sponsored financial benefit message. The message can include the service provider sponsored financial benefit amount and the message may be inserted into a text field of the adjudicated prescription claim request response 208. Alternatively, the message can be appended or otherwise electronically transmitted with the adjudicated prescription claim request response 208.

In step 332, the service provider computer 104 electronically transmits the adjudicated prescription claim request response 208 to the healthcare provider computer 102. In one exemplary embodiment, the adjudicated prescription claim request response 208 includes the service provider sponsored financial benefit message and is electronically transmitted to the healthcare provider computer 102 from the service provider computer 104 via the network 110. The healthcare provider computer in step 334 receives the adjudicated prescription claim request response 208. In step 336, if the adjudicated prescription claim request response 208 was approved/paid and the parties agree to the financial requirements set forth, the pharmacist or other pharmacy employee may dispense the medication to the patient. The process then continues to the END step.

If however, in step 326, the adjudicated prescription claim request response 206 is not eligible for a service provider sponsored financial benefit, a third-party financial benefit may be available for the treatment selection identified in step 324. For example, in step 338 the patient copay assistance module 146 or another portion of the service provider computer 104 may determine if the treatment selection identified in step 324 is eligible for a third-party financial benefit. In one implementation, the patient copay assistance module 146 or another portion of the service provider computer 104 may determine whether the drug identifier associated with the identified treatment selection corresponds to one or more drug identifiers in one or more third-party financial benefit tables and/or lists stored in database 148 and/or data files 136. In one example implementation, the patient copay assistance module 146 may access the third-party financial benefit tables and/or lists and compare the treatment selection (e.g., utilizing an NDC code) with one or more drug identifiers in the third-party financial benefit tables and/or lists. In one implementation, the patient copay assistance module 146 or another portion of the service provider computer 104 may perform the comparison automatically. That is, upon a determination at step 326 that no service sponsored financial benefit is available, the patient copay assistance module 146 or another portion of the service provider computer 104 may automatically access the third-party financial benefit tables and/or lists in search of a financial benefit. Alternatively and/or additionally, a determination at step 326 that no service provider financial benefit is available for the identified treatment selection, the service provider may generate a message indicating the failure to identify a service provider sponsored financial benefit and electronically transmit that message to the healthcare provider computer 102. The service provider computer 104 may, for example, wait to receive a new and/or modified healthcare request from the healthcare provider computer including a request for the service provider computer 104 to query the one or more third-party financial benefit tables and/or lists. In one example implementation, the patient copay assistance module 146 or another portion of the service provider computer 104 may identify the NDC to correspond to the drug Granix™ The patient copay assistance module 146 may compare the NDC for the drug Granix™ to the one or more third-party benefit tables and/or lists to determine if a financial benefit is available for the drug. In one implementation, the one or more third-party benefit tables and/or lists are organized according to product and/or service identifiers (e.g., NDC). A match between the drug identifier corresponding to the identified treatment selection and a drug identifier in the one or more drug identifiers found in the one or more third-party financial benefit tables and/or lists may indicate the availability of at least one financial benefit (e.g., the availability of co-pay savings/reduction, standard co-pay saving cards, or other discount cards such as a first fill free associated with a specific treatment for the illness/disease, a fixed or percentage amount for a voucher, coupon, or discount available to the patient, etc.) associated with the treatment selection identified in the adjudicated prescription claim request response 206. If the third-party financial benefit tables and/or lists include a match corresponding to the drug identifier associated with the identified treatment selection, the treatment selection is eligible for third-party adjudication and the YES branch is followed and processing may proceed to step 340. However, if it is determined that the third-party financial benefit tables and/or lists do not include a match corresponding to the drug identifier associated with the identified treatment selection, then the treatment selection is not eligible for third-party adjudication and the NO branch is followed and processing may proceed to step 354.

In step 340, the patient copay assistance module 146 or another portion of the service provider computer 104 may electronically transmit the adjudicated prescription claim request response 206 to a third-party processor computer 108. In one implementation, the third-party processor computer is identified based upon a third-party identifier found in the third-party financial benefit tables and/or lists stored in database 148 and/or data files 136. For example, the match from step 338 may identify a third-party processor computer (e.g., a coupon card processor) authorized to apply a third-party financial benefit (e.g., a copay assistance) to the adjudicated prescription claim request response 206.

In step 342, the third-party processor computer 106 may ascertain the third-party financial benefit from the one or more third-party financial benefits tables and/or lists and apply the financial benefit(s) (e.g., copay reductions, coupons, vouchers, standard copay saving cards, other discount cards, etc.) to the adjudicated prescription claim request response 210. For example, the third-party financial benefit may include a benefit to reduce and/or eliminate a patient copay amount owing for the identified treatment selection (e.g. Granix™). The third-party processor computer 108 may apply the financial benefit to the adjudicated prescription claim request response 206. For example, where the third-party financial benefit reduces and/or eliminates the patient copay amount, the third-party processor computer 108 may modify the adjudicated prescription claim request response 206 to reflect the third-party financial benefit.

In step 344, the third-party processor computer 106 may communicate the adjudicated prescription claim request response 210 to the service provider computer 104. In step 346, the patient copay assistance module 146 or another portion of the service provider computer 104 may generate a third-party financial benefit message. The message can include the third-party financial benefit amount and the message may be inserted into a text field of the third-party prescription claim request response 210. Alternatively, the message can be appended or otherwise electronically transmitted with the third-party prescription claim request response 210.

In step 348, the service provider computer 104 electronically transmits the adjudicated prescription claim request response 210 to the healthcare provider computer 102. In one exemplary embodiment, the adjudicated prescription claim request response 210 is electronically transmitted to the healthcare provider computer 102 from the service provider computer 104 via the network 110. The healthcare provider computer in step 350 receives the adjudicated prescription claim request response 210. In step 352, if the parties (e.g., patient and pharmacist) agree to the financial requirements set forth in the adjudicated prescription claim request response 210, the pharmacist or other pharmacy employee may dispense the medication to the patient. The process then continues to the END step.

If however, in step 338, the adjudicated prescription claim request response 206 is not eligible for a third-party financial benefit, in step 354 the patient copay assistance module 146 or another portion of the service provider computer 104 may determine if the treatment selection identified in step 324 is eligible for patient reimbursement support. For example, the patient copay assistance module 146 or another portion of the service provider computer 104 may compare the drug identifier (e.g., NDC) associated with the identified treatment selection with one or more patient reimbursement support tables and/or lists stored in database 148 and/or data files 136. In one example, the comparison is made based upon a query sent by the patient copay assistance module 146 or another portion of the service provider computer 104 to database 148 and/or data files 136. In one example implementation, the query may include a comparison between one or more drug identifiers in the one or more patient reimbursement support tables and/or lists with the drug identifier associated with the identified treatment selection. In one example implementation, the one or more patient reimbursement support tables and/or lists include any and all of the various financial assistance available for each drug/product available in the healthcare market. If a match corresponding to the drug identifier associated with the identified treatment selection exists in the one or more patient reimbursement support tables and/or lists, the treatment selection is eligible for a financial benefit and the YES branch is followed and processing may proceed to step 356. However, if it is determined that no match for the drug identifier associated with the identified treatment selection exists in the one or more patient reimbursement support tables and/or lists, then the treatment selection is not eligible for a financial benefit and the NO branch is followed and processing may proceed to step 368.

In step 356, the patient copay assistance module 146 or another portion of the service provider computer 104 may compile the patient reimbursement support from the one or more patient reimbursement support tables and/or lists stored in the database 148 and/or the data files 136. The compilation may include, without limitation, the amount of financial assistance available, sponsor of the financial assistance, access information to obtain the financial assistance (e.g., a website link, a phone number, an address, an email address, etc.), and the like.

In step 358, the patient copay assistance module 146 or another portion of the service provider computer 104 may generate a patient support benefit message. The message can include the patient support financial benefit amount, the sponsor of the financial assistance, access information to obtain the financial assistance (e.g., a website link, a phone number, an address, an email address, etc.), and the like. Alternatively, the message may state that there was no patient reimbursement support available for the identified treatment selection. The message may be inserted into a text field of the adjudicated prescription claim request response 212. Alternatively, the message can be appended or otherwise electronically transmitted with the adjudicated prescription claim request response 212.

In step 360, the service provider computer 104 electronically transmits the adjudicated prescription claim request response 212 to the healthcare provider computer 102. In one exemplary embodiment, the adjudicated prescription claim request response 212 is electronically transmitted to the healthcare provider computer 102 from the service provider computer 104 via the network 110. The adjudicated prescription claim request response 212 is received by the healthcare provider computer in step 362.

In step 364, the pharmacist associated with the healthcare provider computer 102 may review the available patient reimbursement support with the patient. For example, the pharmacist may review all of the information received with the request 212 (e.g., the amount of financial assistance available, sponsor of the financial assistance, access information to obtain the financial assistance (e.g., a website link, a phone number, an address, an email address, etc.), and the like) with the patient. Alternatively and/or additionally, if more than one patient reimbursement support options are available to the patient for the identified treatment selection, the pharmacist may review each available patient reimbursement support option with the patient.

In step 366, the patient may determine whether to opt in to one or more of the patient reimbursement support options. If the patient decides to opt out of one or more patient reimbursement support options, the NO branch and processing may proceed to step 368. However, if the patient opts in to at least one patient reimbursement support option, the YES branch is followed and processing may proceed to step 370.

At step 368, if the parties (e.g., patient and pharmacist) agree to the financial requirements set forth in the adjudicated prescription claim request response 212, the pharmacist or other pharmacy employee may dispense the medication to the patient. The process then continues to the END step.

In step 368, a pharmacist via the healthcare provider computer 102 may auto enroll the patient into the one or more patient reimbursement support options selected by the patient. For example, a patient may select a patient reimbursement support option that reduces and/or eliminates the patient copay amount. Alternatively and/or additionally, the patient reimbursement support option may be selected by the pharmacist or pharmacy employee associated with the healthcare provider computer 102. For example, the pharmacist may select the patient reimbursement support option that provides the patient with the greatest monetary benefit. For example, the pharmacist may select an option that reduces and/or eliminates a patient copay amount.

At step 370, a secondary prescription claim request 214 reflecting the selected patient reimbursement support option is generated and/or formatted at the healthcare provider computer 102. In certain exemplary embodiments, the healthcare provider computer 102 formats the secondary prescription claim request 214 similar to that of the prescription claim request 204. For example, secondary prescription claim request 214 may be formatted in accordance with a version of the National Council for Prescription Drug Programs (NCPDP) Telecommunication Standard, although other standards may be utilized as well.

As discussed above, the secondary prescription claim request 214 may include a BIN Number, a BIN Number and PCN, and/or a BIN Number and Group ID for identifying a particular claims processor computer (e.g., PBM, healthcare insurance company, Medicare or other government healthcare insurance payor, Medicare Part D provider, etc.), such as the claims processor computer 106, as a destination for the secondary prescription claim request 214. In addition, the secondary prescription claim request 214 may also include information relating to the patient, payor, prescriber, healthcare provider, and/or the requested product (e.g., medication or device) or service. As an example, the secondary prescription claim request 214 may include one or more of the following information:

Payor identifier—Payor ID/Routing Information
BIN Number (i.e. Banking Identification Number), BIN Number and Processor Control Number (PCN) and/or BIN Number and Group ID, that designates a destination (e.g., the claims processor computer 106) of the prescription claim request 204
Patient Information
Name (e.g. Patient Last Name, Patient First Name, etc.)
Date of Birth of Patient
Age of Patient
Gender
Patient Address (e.g. Street Address, Zip Code, etc.)
Patient Contact Information (e.g. patient telephone number, email address, etc.)
Patient Health Condition Information
Patient ID or other identifier (e.g., Health Insurance Claim Number (HICN), social security number, etc.)
Insurance/Coverage Information
Cardholder Name (e.g. Cardholder First Name, Cardholder Last Name)
Cardholder ID and/or other identifier (e.g. person code)
Group ID and/or Group Information
Prescriber Information
Primary Care Provider ID or other identifier (e.g. NPI code)
Primary Care Provider Name (e.g. Last Name, First Name)
Prescriber ID or other identifier (e.g. NPI code, DEA number)
Prescriber Name (e.g. Last Name, First Name)
Prescriber Contact Information (e.g. Telephone Number)
Pharmacy Information
Pharmacy or other Healthcare Provider Information (e.g. store name, store address, chain identifier, etc.)
Pharmacy or other Healthcare Provider ID (e.g. NPI code)
Claim Information
Medication, service, or product information—Product (medication or device) or service identifier (e.g. National Drug Code (NDC code), RxNorm code, etc.), product or service name, etc.
Prescription/Service Reference Number
Date Prescription Written
Quantity Dispensed
Days' Supply
Diagnosis/Condition (e.g., diagnosis code)
Pricing information for the drug/service/product (e.g. ingredient cost (e.g., in an Ingredient Cost field), dispensing fee (e.g., in a Dispensing Fee field), gross amount due (e.g., in a Gross Amount Due field), and Usual and Customary Charge amount (e.g., in a Usual and Customary Charge field))
Patient reimbursement benefit identified and applied in Step 368
Number of Refills Authorized
Fill Number (i.e., the current refill number for the current request 204)
One or more NCPDP Message Fields
One or more Drug Utilization (DUR) Codes
Date of Service.

The secondary prescription claim request 214 can be used to determine if the pharmacy claims processor associated with the claims processor computer 106 approves or rejects payment coverage for the prescribed product (e.g., medications, devices, etc.) or service being requested in the secondary prescription claim request 214 and, if approved, the amount the pharmacy claims processor will cover (or pay) for the prescribed product (e.g., medication, device, etc.) or service being requested and how much the patient pay amount (the amount the patient is responsible to pay for) will be.

The healthcare provider computer 102 electronically transmits the secondary prescription claim request 214 to the service provider computer 104 in step 372. In step 374, the service provider computer 104 receives the secondary prescription claim request 214. For example, the secondary prescription claim request 214 can be electronically transmitted by the healthcare provider computer 102 to the service provider computer 104 through the network 110.

At step 376, the service provider computer 104 can parse the received secondary prescription claim request 214 to determine the destination of the secondary prescription claim request 214 (e.g., based on the Banking Identification Number (BIN Number), the BIN Number and Processor Control Number (PCN) or the BIN Number and Group ID in one or more fields of the secondary prescription claim request 214).

The service provider computer 104 electronically transmits the secondary prescription claim request 214 to the claims processor computer 106 in step 378. For example, a secondary prescription claim request 214 can be electronically transmitted from the service provider computer 104 to the claims processor computer 106 via the network 110. The claims processor computer 106 receives and adjudicates the prescription claim request 204 in step 380 to determine if the patient has coverage, to determine to what extent the patient's coverage covers the requested product or service identified in the secondary prescription claim request 214, and to generate an secondary adjudicated claim prescription request response 216 as to whether the secondary prescription claim request 214 is approved/paid or rejected. Example request responses in the secondary adjudicated prescription claim request response 216 can include, but are not limited to, accepted, approved, paid, captured, denied (e.g., rejected), and denied (e.g., rejected) with request for additional information and resubmission. In certain exemplary embodiments, the request responses can be input into a field of the secondary prescription claim request 214 that is recognized by the service provider computer 104 and/or the healthcare provider computer 102. Typically, if the request response for the secondary prescription request 214 is approved, the secondary adjudicated prescription claim request response 216 provides the amount of the cost of the medication, product, or service that will be covered by the pharmacy claims processor associated with the claims processor computer 106 (the total amount paid, which is provided in the Total Amount Paid field of the secondary adjudicated prescription claim request response 216), any amount applied to a patient deductible which is provided in the amount applied to periodic deductible field of the adjudicated prescription claim request response 206), and the patient pay amount (which is provided in the Patient Pay Amount field of the secondary adjudicated prescription claim request response 216 and may be modified according to one or more patient reimbursement financial benefits identified at step 354). On the other hand, if the request response is a rejection, the secondary adjudicated prescription claim request response 216 provides the reason for the rejection (e.g., in the form of a reject code, for example, patient not covered, Cardholder ID submitted in the request is inactive, prior authorization required, medication not covered, claim limit exceeded, quantity exceeded, days' supply exceeded, etc.).

In step 382, the claims processor computer 106 electronically transmits the secondary adjudicated prescription claim request response 216 to the service provider computer 104 via, for example, the network 110. The service provider computer 104 receives the secondary adjudicated prescription claim request response 216 from the claims processor computer 106 in step 384. In step 386, the service provider computer 104 electronically transmits the secondary adjudicated prescription claim request response 216 to the healthcare provider computer 102. In one exemplary embodiment, the secondary adjudicated prescription claim request response 216 is electronically transmitted to the healthcare provider computer 102 from the service provider computer 104 via the network 110. The secondary adjudicated prescription claim request response 216 is received by the healthcare provider computer in step 388. In step 390, if the parties (e.g., patient and pharmacist) agree to the financial requirements set forth in the secondary adjudicated prescription claim request response 216, the pharmacist or other pharmacy employee may dispense the medication to the patient. The process then continues to the END step.

The methods described and shown in FIGS. 3A-C may be carried out or performed in any suitable order as desired in various embodiments. Additionally, in certain exemplary embodiments, at least a portion of the operations may be carried out in parallel. Furthermore, in certain exemplary embodiments, less than or more than the operations described in FIGS. 3A-C may be performed.

Figure 2B:
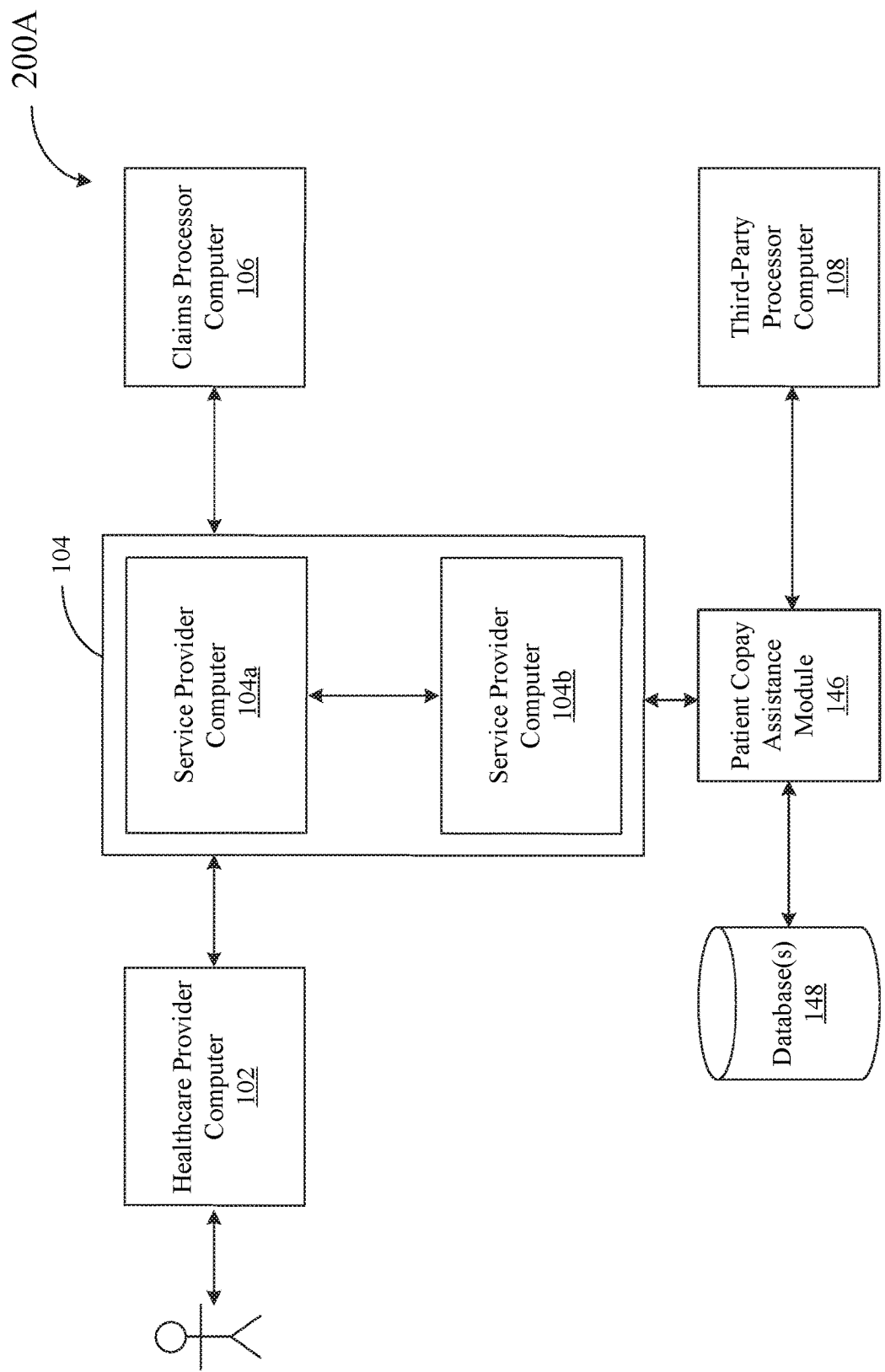
FIG. 2B is a diagram of another example system flow for the improved medical delivery system according to an alternative exemplary embodiment.

Likewise, while FIGS. 3A-C have been described primarily in conjunction with FIG. 2A, it will be appreciated that variations of FIG. 2A are available. As shown by the system 200A of FIG. 2B, the service provider computer 106 may include two or more distinct service provider computers 104a and 104b that are in communication with each other. These distinct service provider computers 104a and 104b may be owned, operated, and/or located by the same or distinct and wholly-unrelated companies. The service provider computer 104a may be operative with the healthcare provider computer 102, while the service provider computer 104b may be operative with other healthcare provider computers and/or other third-party entity computers. However, the service provider computer 104b may have a data processing arrangement with the service provider computer 104a. Under the data processing arrangement, the service provider computer 104a may be permitted to utilize or financial benefit identification services of the service provider computer 104b, including the operations and use of the patient copay assistance module 146 and the data in the database 148 to identify financial benefits, as discussed above. Accordingly, the services accessible by the service provider computer 104b, may be available to the healthcare provider computer 102 via the service provider computers 104a and 104b.

While certain example embodiments disclosed herein describe the patient copay assistance module 146 as being separate of the service provider computer 104, in alternate embodiments, the patient copay assistance module 146 or the functions that it completes may be part of the service provider computer 104. In those embodiments where the patient copay assistance module 146 is incorporated into the service provider computer 104, and with regard to the methods described above, the elements describing transmitting or receiving between the service provider computer 104 and the patient copay assistance module 146 may be internal transmissions within the service provider computer 104 or may be omitted altogether. Further, while the exemplary embodiments described herein disclose certain steps occurring at the service provider computer 104 and/or the patient copay assistance module 146, in alternative embodiments those steps described with reference to FIGS. 1-3C may alternately be completed at a healthcare provider computer 102, a claims processor computer 106, a third-party processor computer 108, a patient copay assistance module 146, any combination thereof, and/or a combination of those devices along with the service provider computer 104. In those alternate embodiments, certain transmission/receiving blocks described above with reference to FIGS. 1-3C may be omitted while others may be added, as understood by one or ordinary skill in the art. The intent being that, in alternate embodiments, any of the devices/computers discussed in FIG. 1 are capable of completing all or any part of the methods described with reference to FIGS. 2A-3C.

Accordingly, example embodiments disclosed herein can provide the technical effects of creating a system and method that provides real-time or near real time way to facilitate the selection and application of patient financial assistance for a prescribed product based on an inquiry of available financial benefits as part of or in-line with the processing of one or more types of healthcare claim requests. In this regard, pharmacies will continue to be able to provide prescribed medications within claim processing parameters for a product and/or service with an automatic application of a financial benefit to the prescription claim thus reducing the risk that a patient would not receive financial assistance at the point of purchase.

Although example embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component that is properly configured. Furthermore, while various example implementations and architectures have been described in accordance with example embodiments of the disclosure, one of ordinary skill in the art will appreciate that numerous other modifications to the example implementations and architectures described herein are also within the scope of this disclosure.

Certain aspects of the disclosure are described above with reference to block and flow diagrams of systems, methods, apparatuses, and/or computer program products according to example embodiments. It will be understood that one or more blocks of the block diagrams and steps of the flow diagrams, and combinations of blocks in the block diagrams and steps of the flow diagrams, respectively, may be implemented by execution of computer-executable program instructions. Likewise, some blocks of the block diagrams and steps of the flow diagrams may not necessarily need to be performed in the order presented, or may not necessarily need to be performed at all, according to some embodiments. Further, additional components and/or operations beyond those depicted in blocks of the block and/or steps of the flow diagrams may be present in certain embodiments.

Accordingly, blocks of the block diagrams and steps of the flow diagrams support combinations of means for performing the specified functions, combinations of elements or steps for performing the specified functions and program instruction means for performing the specified functions. It will also be understood that each block of the block diagrams and step of the flow diagrams, and combinations of blocks in the block diagrams and steps of the flow diagrams, are implemented by special-purpose, hardware-based computer systems that perform the specified functions, elements or steps, or combinations of special-purpose hardware and computer instructions.

Computer-executable program instructions may be loaded onto a special-purpose computer or other particular machine, a processor, or other programmable data processing apparatus to produce a special-purpose machine, such that execution of the instructions on the computer, processor, or other programmable data processing apparatus causes one or more functions or steps specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or steps specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program modules, or other data transmitted within a data signal, such as a carrier wave, or other transmission. However, as used herein, CRSM does not include CRCM.

Although example embodiments have been described in language specific to structural features and/or methodological acts, it is to be understood that the disclosure is not necessarily limited to the specific features or acts described. Rather, the specific features and acts are disclosed as illustrative forms of implementing the example embodiments. Conditional language, such as, among others, "can," "could," "might," or "may," unless specifically stated otherwise, or otherwise understood within the context as used, is generally intended to convey that certain example embodiments could include, while other example embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

What is claimed is:

1. A system comprising;
at least one memory operable to store computer-executable instructions; and
at least one processor configured to access the at least one memory and execute the computer-executable instructions to:
receive by a network interface of a service provider computer, from at least one healthcare provider computer of a plurality of healthcare provider computers in a network, a prescription claim request;
access a routing table stored by the service provider computer embodied by a switch or a router to determine a claims processor computer to which to transmit the prescription claim request;
transmit the prescription claim request to the claims processor computer over the network;
receive, from the claims processor computer, an adjudicated prescription claim request in response to the prescription claim request, wherein the adjudicated prescription claim request comprises a patient amount owing field;
with a patient copay assistance module implemented by the service provider computer, evaluate the adjudicated prescription claim request response for one or more financial benefits, the evaluation comprising:
identify a product identifier for a product/service being requested in the prescription claim request;
compare the product identifier with one or more product/service identifiers in a first financial benefit table;
determine, based on the comparison, that the product identifier does not match the one or more product/service identifiers in the first financial benefit table;
based upon a negative determination that a match exists in the first benefit table, automatically access a second financial benefit table to determine whether a second financial benefit is available;
based upon a negative determination that a match exists in the second benefit table, automatically access a third financial benefit table to identify a third financial benefit;
in an instance the third financial benefit reflects a copay amount that is reduced or, eliminated relative to a copay amount of the adjudicated prescription claim request response, generate by the at least one processor, and store on the at least one memory, a patient support benefit message comprising at least a plurality of patient support financial benefit amounts corresponding to respective financial benefit programs;
access the routing table to determine a pharmacy computer to which the patient support benefit message is to be routed;
transmit the patient support benefit message to the pharmacy computer over the network, the patient support benefit message comprising the plurality of patient support financial benefit amounts corresponding to the respective financial benefit programs;
receive an indication of a selection of at least one of the plurality of financial benefit programs; and
in response to receiving the indication of the selection of the at least one of the plurality of financial benefit programs, auto-enroll the patient in the selected one of the at least one of the plurality of financial benefit programs, generate a secondary prescription claim request reflecting the selected financial benefit program, and transmit the secondary prescription claim request for adjudication to the claims processor computer.

2. The system of claim 1, wherein the processor configured to automatically access a third financial benefit table is further configured to access the at least one memory and execute the computer-executable instructions to:
compile a list of one or more financial benefits identified for the product/service identified in the prescription claim request; and
receive, from the pharmacy computer, a secondary prescription claim request, wherein a patient payment amount within the secondary prescription claim request includes the patient support financial benefit amount.

3. The system of claim 2, wherein the third financial benefit table is a patient reimbursement support table comprising one or more patient reimbursement financial benefits, and wherein the compilation of one or more financial benefits identified for the product/service identified in the prescription claim request comprises at least one of a patient reimbursement amount available, a sponsor of the patient reimbursement financial benefit, or access information to obtain the patient reimbursement financial benefit.

4. The system of claim 3, wherein the patient support message further comprises the access information to obtain the patient reimbursement financial benefit.

5. The system of claim 1, wherein the processor configured to automatically access the second financial benefit table to determine whether a second financial benefit is available is further configured to, based upon a positive determination that a second financial benefit is available, access the at least one memory and execute the computer-executable instructions to:
direct communication of the adjudicated prescription claim request to a third-party processor computer for modification;
receive, from the third-party processor computer, a modified adjudicated prescription claim request response, wherein the modification comprises a modified patient amount owing field for the product/service identified in the prescription claim request;
generate a third-party financial benefit message comprising at least a third-party financial benefit amount;
modify the modified adjudicated prescription claim request response to include the third-party financial benefit message; and
direct communication of the modified adjudicated prescription claim request response to a pharmacy computer for a pharmacy for dispensation of the product/service to a patient identified in the prescription claim request.

6. The system of claim 4, wherein the second financial benefit table comprises a field comprising a third-party processor computer identifier utilized to direct communication of the adjudicated prescription claim request for modification.

7. The system of claim 1, wherein the patient amount owing field comprises data indicating a patient copay amount.

8. The system of claim 1, wherein the first financial benefit table is a service provider sponsored benefit table comprising one or more service provider sponsored financial benefits, wherein a service provider sponsored financial benefit comprises at least one of an incentive program, a coupon, a voucher, a rebate, a discount, or a loyalty award.

9. The system of claim 1, wherein the processor configured to evaluate the adjudicated prescription claim request response for one or more financial benefits is further configured to access the at least one memory and execute the computer-executable instructions to:
query the first financial benefit table to determine whether the product identifier in the prescription claim request matches at least one of a plurality of product identifiers in the first financial benefit table.

10. The system of claim 1, wherein the product identifier in the prescription claim request is an NDC code, and wherein the first benefit table, the second benefit table, and the third benefit table all comprise one or more NDC codes.

11. A computer-implemented method for improved medical delivery, comprising:
receiving by a network interface of a service provider computer, from at least one healthcare provider computer of a plurality of healthcare provider computers in a network, a prescription claim request;
accessing a routing table stored by the service provider computer embodied by a switch or a router to determine a claims processor computer to which to transmit the prescription claim request;
transmitting the prescription claim request to the claims processor computer over the network;
receiving, by the service provider computer from the claims processor computer, an adjudicated prescription claim request in response to the prescription claim request, wherein the adjudicated prescription claim request comprises at least a patient amount owing field;
with a patient copay assistance module implemented by the service provider computer, evaluating, by the service provider computer, the adjudicated prescription claim request for one or more financial benefits, the evaluation comprising:
identifying, by the service provider computer, a product identifier for a product/service being requested in the prescription claim request;
comparing, by the service provider computer, the product identifier with one or more product/service identifiers in a first financial benefit table;
determining, by the service provider computer and based on the comparison, that the product identifier does not match the one or more product/service identifiers in the first financial benefit table;
based upon a negative determination that a match exists in the first benefit table, automatically, by the service provider computer, accessing a second financial benefit table to determine whether a second financial benefit is available;
based upon a negative determination that a match exists in the second benefit table, automatically, by the service provider computer, accessing a third financial benefit table to identify a third financial benefit;
in an instance the third financial benefit reflects a copay amount that is reduced or eliminated relative to a copay amount of the adjudicated prescription claim request response, generating with a processor, and storing, on a memory device, a patient support benefit message comprising at least a plurality of patient support financial benefit amounts corresponding to respective financial benefit programs;
accessing the routing table to determine a pharmacy computer to which the patient support benefit message is to be routed;
transmitting the patient support benefit message to the pharmacy computer over the network, the patient support benefit message comprising the plurality of patient support financial benefit amounts corresponding to the respective financial benefit programs;

receiving an indication of a selection of at least one of the plurality of financial benefit programs; and in response to receiving the indication of the selection of the at least one of the plurality of financial benefit programs, auto-enrolling the patient in the selected one of the at least one of the plurality of financial benefit programs, generating a secondary prescription claim request reflecting the selected financial benefit program, and transmitting the secondary prescription claim request for adjudication to the claims processor computer.

12. The computer-implemented method of claim 11, wherein automatically accessing a third financial benefit table to identify a third financial benefit further comprises:

compiling, by the service provider computer, a list of one or more financial benefits identified for the product/service identified in the prescription claim request; and receiving, by the service provider computer from the pharmacy computer, a secondary prescription claim request, wherein a patient payment amount within the secondary prescription claim request includes the patient support financial benefit amount.

13. The computer-implemented method of claim 12, the third financial benefit table is a patient reimbursement support table comprising one or more patient reimbursement financial benefits, and wherein the compilation of one or more financial benefits identified for the product/service identified in the prescription claim request comprises at least one of a patient reimbursement amount available, a sponsor of the patient reimbursement financial benefit, or access information to obtain the patient reimbursement financial benefit.

14. The computer-implemented method of claim 13, wherein the patient support message further comprises the access information to obtain the patient reimbursement financial benefit.

15. The computer-implemented method of claim 11, wherein automatically access the second financial benefit table to determine whether a second financial benefit is available further comprises:

transmitting, by the service provider computer, the adjudicated prescription claim request to a third-party processor computer for modification;

receiving, by the service provider computer from the third-party processor computer, a modified adjudicated prescription claim request response, wherein the modification comprises a modified patient amount owing field for the product/service identified in the prescription claim request;

generating, by the service provider computer, a third-party financial benefit message comprising at least a third-party financial benefit amount;

modifying, by the service provider computer, the modified adjudicated prescription claim request response to include the third-party financial benefit message; and transmitting, by the service provider computer, the modified adjudicated prescription claim request response to a pharmacy computer for a pharmacy for dispensation of the product/service to a patient identified in the prescription claim request.

16. The computer-implemented method of claim 15, wherein the second financial benefit table comprises a field comprising a third-party processor computer identifier utilized to direct communication of the adjudicated prescription claim request for modification.

17. The computer-implemented method of claim 11, wherein the patient amount owing field is a patient copay amount.

18. The computer-implemented method of claim 11, wherein the first financial benefit table is a service provider sponsored benefit table comprising one or more service provider sponsored financial benefits, wherein a service provider sponsored financial benefit comprises at least one of an incentive program, a coupon, a voucher, a rebate, a discount, or a loyalty award.

19. The computer-implemented method of claim 11, wherein evaluating the adjudicated prescription claim request response for one or more financial benefits comprises querying, by the service provider computer, the first financial benefit table to determine whether the product identifier for the product/service being requested by the patient exists in the first financial benefit table.

20. The computer-implemented method of claim 11, wherein the product identifier for the one or more product/service identifiers in the prescription claim request is an NDC code, and wherein the first benefit table, the second benefit table, and the third benefit table all comprise one or more NDC codes.

* * * * *